United States Patent

Ohtsu et al.

[11] Patent Number: 5,976,511
[45] Date of Patent: Nov. 2, 1999

[54] ULTRAVIOLET RAYS-ABSORBING COMPOSITION AND PROCESS FOR PRODUCING THE SAME

[75] Inventors: Koichi Ohtsu; Noriaki Sato, both of Fukushima, Japan

[73] Assignee: Sakai Chemical Industry Co., Ltd., Osaka, Japan

[21] Appl. No.: 08/973,819

[22] PCT Filed: Jun. 21, 1996

[86] PCT No.: PCT/JP96/01731

§ 371 Date: Dec. 11, 1997

§ 102(e) Date: Dec. 11, 1997

[87] PCT Pub. No.: WO97/40118

PCT Pub. Date: Oct. 30, 1997

[30] Foreign Application Priority Data

Apr. 25, 1996  [JP]  Japan .................................. 8-131317
Jun. 10, 1996  [JP]  Japan .................................. 8-171883

[51] Int. Cl.$^6$ .............................. A61K 7/42; A61K 7/00; C09C 1/02; C01F 11/46
[52] U.S. Cl. ........................... 424/59; 106/461; 106/471; 423/554; 424/60; 424/69; 424/400; 424/401
[58] Field of Search ................................ 424/59, 60, 400, 424/401, 69; 423/554; 106/461, 471

[56] References Cited

U.S. PATENT DOCUMENTS 5,171,572  12/1992  Suganuma et al. ..................... 424/401
5,262,148  11/1993  Sugasawa et al. ..................... 423/554

FOREIGN PATENT DOCUMENTS 0256417   2/1988   European Pat. Off. .
0266247   5/1988   European Pat. Off. .
0565043   10/1993  European Pat. Off. .
4120747   1/1993   Germany .
48-56833  8/1973   Japan .
5-39436   2/1993   Japan .
6-145022  5/1994   Japan .

OTHER PUBLICATIONS

Database WPI, Week 8311, Derwent Publications Ltd., London, GB; AN 83–26601k, XP002066138; and JP 58 021 455 A (Kubo Y.), Feb. 8, 1983 (abstract).
Database WPI, Week 9242, Derwent Publication Ltd., London, GB, AN 92–345112, XP002066139; and JP 04 249 584 A (Tayca Corp.) Sep. 4, 1992 (abstract).
Patent Abstracts of Japan, vol. 13, No. 487, (C–649), Nov. 6, 1989; and JP 01 190626A (Catalysts & Chem. Ind. Co.), Jul. 31, 1989 (abstract).

*Primary Examiner*—Shelley A. Dodson
*Attorney, Agent, or Firm*—Sughrue, Mion, Zinn, Macpeak & Seas, PLLC

[57] ABSTRACT

The invention provides an ultraviolet rays-absorbing composition having a pearly luster which comprises plate barium sulfate particles having a surface coated with at least one of zinc oxide, cerium oxide and titanium oxide and a process for preparing the same. The composition has a pearly luster of stable quality, satisfactory translucence, and a satisfactory feel.

7 Claims, 7 Drawing Sheets

10 μm

ULTRAVIOLET RAYS-ABSORBING COMPOSITION AND PROCESS FOR PRODUCING THE SAME

TECHNICAL FIELD

The present invention relates to an ultraviolet rays-absorbing composition and a process for producing the same. The ultraviolet rays-absorbing composition according to the present invention has a pearly luster and is very useful as a component of make-up cosmetics, coatings and the like.

BACKGROUND ART

Ultraviolet rays included in sunlight reaching the ground adversely affect the human body such as the skin, buildings such as houses, and the like so that various countermeasures for shielding ultraviolet rays have been proposed. While ultraviolet rays are divided into A region (wavelength of 320 to 380 nm) and B region (wavelength of 290 to 320 nm) according to Commission Internationale de l'Eclairage (CIE), it is of great concern that the amount of ultraviolet rays reaching the ground have recently been increasing with the decomposition of the ozonosphere by flon and the like. Furthermore, while the conventional target of shielding ultraviolet rays has been confined to B region, it has recently been revealed that the ultraviolet rays of A region penetrates deep into the skin to damage the tissue and accelerate skin aging. Therefore, not only B region but also A region have been attracting attention as a target of shielding ultraviolet rays.

Ultraviolet rays-absorbing compositions conventionally used in cosmetic sunscreens, ultraviolet rays-shielding coatings and the like mainly comprise organic compounds, such as benzophenone compounds, benzoic acid derivatives or the like. Since these organic compounds show absorption bands generally in the range of from 280 to 350 nm, the ultraviolet rays of A region cannot be completely shielded.

Additionally ultraviolet rays-absorbing compositions comprising organic compounds are problematical from the standpoint of safety to the human body.

Inorganic pigments showing broader ultraviolet rays-absorption bands have also been used in place of the organic compounds. In particular, a cosmetic composition or a coating composition containing ultrafine particles having an average primary particle size of 0.1 µm or less forms a translucent coating film with a natural tone. Of these inorganic pigments, titanium oxide has enjoyed the most frequent use because it completely shields ultraviolet rays having a wavelength of 360 nm or shorter.

In recent years, zinc oxide has attracted attention as disclosed in JP-B-7-23294. Zinc oxide exhibits a still broader ultraviolet rays-absorption band than titanium oxide and completely shields ultraviolet rays having a wavelength of 370 nm or shorter. Furthermore, the hiding power of zinc oxide is not so high because of its low refractive index ranging from 1.9 to 2.0, so that it gives excellent translucence free from white turbidity when made into ultrafine particles of 0.1 µm or smaller. For use in a coating composition, it can easily be colored. For use in cosmetics, zinc oxide can provide the composition with astringency or an antiinflammatory effect and also has a sebum absorbing effect.

Cerium oxide is known to have an ultraviolet rays-absorbing effect similarly to zinc oxide and titanium oxide. Although cerium oxide does not show a clear absorption end unlike zinc oxide or titanium oxide, it has a still broader absorption band than zinc oxide and titanium oxide and shields ultraviolet rays of 380 nm or shorter. Accordingly, cerium oxide can be used for its ultraviolet rays-absorbing effect similarly to zinc oxide and titanium oxide.

If ultrafine particles of zinc oxide, cerium oxide or titanium oxide are used as a component of cosmetics or coatings, they must be uniformly dispersed in a medium. However, ultrafine particles having a particle size, e.g., of 0.1 µm or smaller readily undergo secondary agglomeration due to their great van der Waals forces. It is difficult to uniformly disperse the coarse secondary particles. Cosmetics, for instance, containing the particles in a non-uniformly dispersed state cannot get rid of color unevenness or an uncomfortable feel to the touch when applied to the skin.

In the field of pigments, pearlescent pigments which not only have a plurality of hues but vary their hue depending on the view angle have been extending their use in cosmetics and the like with the increasing diversity of liking. Pearlescent pigments are prepared by coating plate particles obtained by grinding naturally occurring substances, such as talc, mica, sericite and the like, with metal oxides, such as titanium dioxide, silica, alumina, zirconium oxide, iron oxide and the like.

Various improvements have been added to such pearlescent pigments. For example, JP-A-5-23671 discloses a technique of obtaining an oil-repellent pearlescent pigment which comprises coating mica flakes with titanium dioxide and further treating the surface of the coated flakes with a perfluoroalkylsilane.

JP-A-2-179954 discloses a technique of obtaining a weatherable pearlescent pigment comprising mica flakes having a coat of a solid solution of nickel oxide, cobalt oxide and the like as a color forming material when mica flakes are coated with titanium dioxide.

JP-A-5-17329 proposes a technique of obtaining a highly ultraviolet rays-shielding pearlescent pigment comprising sericite particles having a titanium oxide coat which is further coated with zinc oxide.

Thus, a number of improvements on pearlescent pigments have so far been made, but the techniques using plate particles obtained by grinding naturally occurring materials, such as talc, mica, sericite and the like, as a substrate are unavoidably disadvantageous in that the substrate particles have unevenness in color due to impurities, which results in unevenness in tone of final products. This has made product color control difficult particularly for those products putting weight on color, such as cosmetics.

Furthermore, because they are natural substances, it is difficult to secure a requisite quantity of a substance with stable properties. In particular, sericite has become hardly available. Mica is relatively easy to get, but its cleavage makes it difficult to secure a constant shape as flaky powder.

Hence, it has been proposed to apply flaky powder of barium sulfate which is easy to synthesize to cosmetics.

JP-B-62-34688 discloses a process for producing plate barium sulfate particles regular in size which comprises reacting barium sulfide and sulfuric acid at a molar ratio of 1:1. However, this process provides coarse barium sulfate particles, which are suitable for use as an additive to synthetic resins but are not always satisfactory for use in cosmetics.

JP-B-49-46908 discloses a technique in which a flaky pigment comprising fine plate crystals of barium sulfate having a thin coating film of titanium oxide, zirconium oxide, zinc oxide and the like is used as a component of make-up cosmetics. According to the disclosure, the flaky pigment exhibits a luster and a satisfactory feel to the touch as well as spreadability. However, the term "luster" as used therein is intended to mean the property of allowing the pigment deposited and bound for imparting a color to appear clearly, which is different from a so-called pearly luster.

Based on the above circumstances, an object of the invention is to provide a ultraviolet rays-absorbing composition having constant quality in terms of hue and pearly luster and provides satisfactory translucence and a satisfactory feel. Another object of the invention is to provide a process for producing the composition.

DISCLOSURE OF THE INVENTION

The inventors of the present invention have found that the problems associated with conventional pearly pigments can be successfully solved by coating plate barium sulfate particles with a specific inorganic metal oxide and thus reached the present invention.

That is, the present invention provides an ultraviolet rays-absorbing composition having a pearly luster which comprises plate barium sulfate particles having a surface coated with at least one of zinc oxide, cerium oxide and titanium oxide.

The present invention will be discussed below in detail.

The ultraviolet rays-absorbing composition according to the present invention comprises plate barium sulfate.

The term "plate barium sulfate" as used herein means barium sulfate particles having an aspect ratio of 10 to 150.

The term "aspect ratio" as used herein means a ratio of the diameter of the main plane of a plate particle to the thickness.

The aspect ratio can be determined as follows. A micrograph (A) is taken of barium sulfate particles under a scanning electron microscope. Then, the same particles are turned sideways and photographed from an angle forming 90° to the angle of photograph (A) to obtain a micrograph (B) on which the thickness direction can be observed.

Twenty lines are drawn on micrograph (A) at given intervals, and the lengths of the lines running on the barium sulfate particles are added up, and the sum is divided by the number of particles on which the lines run to obtain an average, which is taken as an average particle diameter (L).

Separately, 20 lines are drawn on micrograph (B) at given intervals. n particles (n is 20 or more) whose thickness direction corresponds to the lines are selected, and the sum of the thicknesses of the n particles is divided by n to obtain an average, which is taken as an average thickness (D).

The value of dividing the above average particle diameter by the above average thickness (L/D) is the aspect ratio.

FIGS. 8 and 9 are each an example of a scanning electron micrograph (×1000) of plate barium sulfate.

From the photographs, it is understood how to obtain the aspect ratio.

The plate barium sulfate for use in the invention preferably has an average particle diameter of 3 to 70 $\mu$m. Particles smaller than 3 $\mu$m in diameter have seriously deteriorated slip properties, particles greater than 70 $\mu$m give a rough feel, and both cannot be used as cosmetics or coatings.

The average particle diameter of the plate barium sulfate can be obtained as the above-mentioned average particle diameter (L).

The plate barium sulfate preferably has an average thickness of 0.05 to 2 $\mu$m. Particles having a thickness smaller than 0.05 $\mu$m or greater than 2 $\mu$m give an uncomfortably rough feel.

The average thickness of the plate barium sulfate can be obtained as the above-mentioned average thickness (D).

The plate barium sulfate can be obtained by reacting barium hydroxide and sulfuric acid.

Plate barium sulfate has generally been prepared from combinations of a soluble barium salt, such as barium sulfide, barium nitrate or the like, and a soluble sulfate, such as sodium sulfate, ammonium sulfate or the like. However, the plate barium sulfate obtained from any of the combinations contains a by-product, such as sodium sulfide or ammonium nitrate, which is hardly removed completely.

On the other hand, the process comprising reacting barium hydroxide and sulfuric acid produces only barium sulfate and water, which is of great industrial advantage. Barium sulfate having extremely high purity can be obtained by using purified starting materials.

The reaction can be carried out either continuously or batchwise. In either case, the reaction is performed by simultaneously and continuously feeding stoichiometric amounts of barium hydroxide and sulfuric acid to a reaction vessel equipped with a stirrer.

The concentration of unreacted barium ions and sulfate ions in the reaction system is adjusted to 0.00001 to 0.005 mol/l. It is practically difficult to adjust to a concentration lower than 0.00001 mol/l. If the concentration exceeds 0.005 mol/l, it is extremely difficult to produce plate barium sulfate particles.

The unreacted ion concentration can be adjusted by controlling the amounts of the starting materials so as to maintain the electrical conductivity at a certain constant value, making use of the correlation between the unreacted ion concentration and electrical conductivity as shown in Table 1 below.

TABLE 1

| Unreacted Ion Concentration (mol/l) | Electrical Conductivity ($\mu$S) | Particle Size ($\mu$m) |
|---|---|---|
| 0.00001 to 0.00005 | 1 to 50 | 20 to 70 |
| 0.00005 to 0.0005 | 50 to 500 | 5 to 30 |
| 0.005 to 0.005 | 500 to 5000 | 3 to 10 |

The concentrations of a barium hydroxide solution and a sulfuric acid solution in the reaction vessel are each 200 g/l or less. If the concentration exceeds 200 g/l, it is difficult to precisely control the unreacted ion concentration. Since too low a concentration is industrial disadvantageous, a preferred concentration is 10 to 200 g/l.

The reaction temperature is preferably not higher than 80° C. If it exceeds 80° C., the produced particles tend to grow in the thickness direction conspicuously, failing to give a smooth feel.

After completion of the reaction, it is preferred to adjust the reaction mixture to a pH of 6.5 to 7.5 by addition of barium hydroxide or sulfuric acid.

The surface of the plate barium sulfate particles thus produced are then coated with at least one of zinc oxide, cerium oxide and titanium oxide to thereby provide an ultraviolet rays-absorbing composition having the ultraviolet rays-absorbing effect possessed by zinc oxide, cerium oxide or titanium oxide as well as the basic characteristics essentially possessed by plate barium sulfate, i.e., translucence, a satisfactory feel to the touch, non-toxicity and the like.

The "at least one of zinc oxide, cerium oxide and titanium oxide" means one, two or three of the three oxides. If two or more thereof are used for coating, they may be in a multilayer state each forming a separate layer.

The total thickness of the coating layer is not particularly limited but is preferably 0.05 to 0.5 $\mu$m, more preferably 0.05 to 0.2 $\mu$m, taking into consideration the balance of the ultraviolet rays-absorbing effect of the coating layer and the characteristics of the plate barium sulfate.

At least one of zinc oxide, cerium oxide and titanium oxide constituting the coating layer preferably has a maximum particle size of not greater than 0.2 $\mu$m and an average particle size of 10 to 150 nm. The limitation on the maximum particle size and the average particle size can be clearly accounted for particularly as for zinc oxide. Zinc oxide particles having such a small size well transmit visible light and have a reduced hiding power and increased transparency to thereby provide an ultraviolet rays-absorbing composition with improved quality. Of the coating oxides, more preferably, titanium oxide has a maximum particle size of not more than 0.1 $\mu$m.

While coating of the plate barium sulfate can be carried out by various techniques, the following method is particularly preferred.

At first, the plate barium sulfate is suspended in water. An aqueous solution of a zinc salt, for instance, is added to the suspension. The zinc salt to be used is not particularly limited and includes zinc sulfate, zinc nitrate, zinc chloride, zinc acetate and the like.

To the suspension is slowly added at least one aqueous solution selected from aqueous ammonia, an alkali hydroxide aqueous solution, an alkali carbonate aqueous solution, an ammonium carbonate aqueous solution, and an ammonium hydrogencarbonate aqueous solution.

As a result, a uniform coating film of zinc hydroxide or zinc carbonate is formed on the surface of the plate barium sulfate.

The coated plate barium sulfate thus produced is collected by filtrating the above solution. The coated plate barium sulfate thus collected can be purified by washing with water and drying.

The resulting coated plate barium sulfate is calcined to convert the zinc hydroxide or zinc carbonate to zinc oxide to obtain zinc oxide-coated plate barium sulfate of the present invention.

The resulting zinc oxide-coated plate barium sulfate is dispersed, e.g., in liquid paraffin, solid paraffin, vaseline or the like, to obtain the ultraviolet rays-absorbing composition of the invention.

Plate barium sulfate having a surface coated with cerium oxide can be prepared in the same manner as described above by using an aqueous solution of a cerium salt. While not limiting, suitable cerium salts include cerium sulfate, cerium nitrate, cerium chloride, cerium acetate and the like.

Plate barium sulfate having a surface coated with titanium oxide can be prepared by adding an aqueous solution of titanyl sulfate or titanium tetrachloride to an aqueous suspension of plate barium sulfate, followed by hydrolysis under heating or addition of at least one alkali solution selected from an alkali hydroxide aqueous solution, aqueous ammonia and an aqueous urea solution.

The resulting coated plate barium sulfate is collected by filtration, washing with water, drying and calcination in the same manner as described above to obtain titanium oxide-coated plate barium sulfate.

Plate barium sulfate having a surface coated with two or more of zinc oxide, cerium oxide and titanium oxide in layers can be prepared by combining the above-mentioned steps appropriately.

For example, the step of forming a zinc oxide layer on plate barium sulfate followed by the step of forming a cerium oxide layer gives plate barium sulfate having a double coating layer with zinc oxide as an inner layer and cerium oxide as an outer layer. The resulting particles can further be subjected to the step of forming a titanium oxide layer to obtain plate barium sulfate having a triple coating layer with titanium oxide as an outermost layer. The order of the three layers can be changed by changing the order of the above-described steps.

On the other hand, plate barium sulfate having a surface coated with a mixture of two or more of zinc oxide, cerium oxide and titanium oxide can be obtained by adding to an aqueous suspension of plate barium sulfate two or three of a zinc salt aqueous solution, a cerium salt aqueous solution, a titanyl sulfate aqueous solution and a titanium tetrachloride aqueous solution, followed by hydrolysis under heating or addition of at least one alkali aqueous solution selected from an alkali hydroxide aqueous solution (e.g., a sodium hydroxide aqueous solution), aqueous ammonia and a urea aqueous solution.

The resulting coated particles are collected by filtration, washing with water, drying and calcination to obtain plate barium sulfate having a mixed coating layer.

If desired, in order to impart water repellency and flowability, the ultraviolet rays-absorbing composition of the invention can be treated with a metallic soap, silicone, a titanate and the like to provide an ultraviolet rays-absorbing composition having an improved smoothness to the feel which is suitable, for example, as cosmetics.

The ultraviolet rays-absorbing composition of the invention has a pearly luster. The pearly luster of the composition can vary from silvery white to a lustrous color tone by controlling the coating thickness of zinc oxide, cerium oxide and/or titanium oxide in relation to the size and specific surface area of the plate barium sulfate particles.

The pearly luster of the ultraviolet rays-absorbing composition comprising the titanium oxide-coated plate barium sulfate has an outstanding effect that cannot be attained with other material-coated plate barium sulfate particles.

The ordinate is a light transmission (%), and the abscissa is a wavelength (nm); S indicates the plate barium sulfate used in Examples 1 to 12; and numerals 1, 2 and 3 indicate powders obtained in Example Nos. 1, 2 and 3, respectively.

Figure 1:
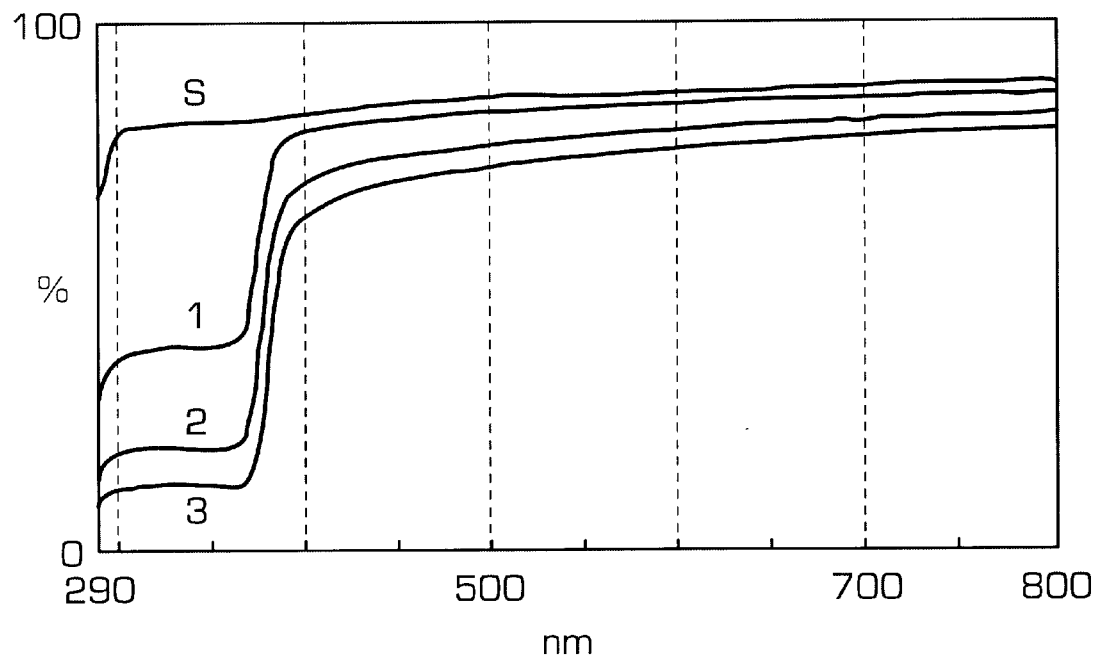
FIG. 1 is a graph of light transmission of the powder obtained in Examples.
Figure 2:
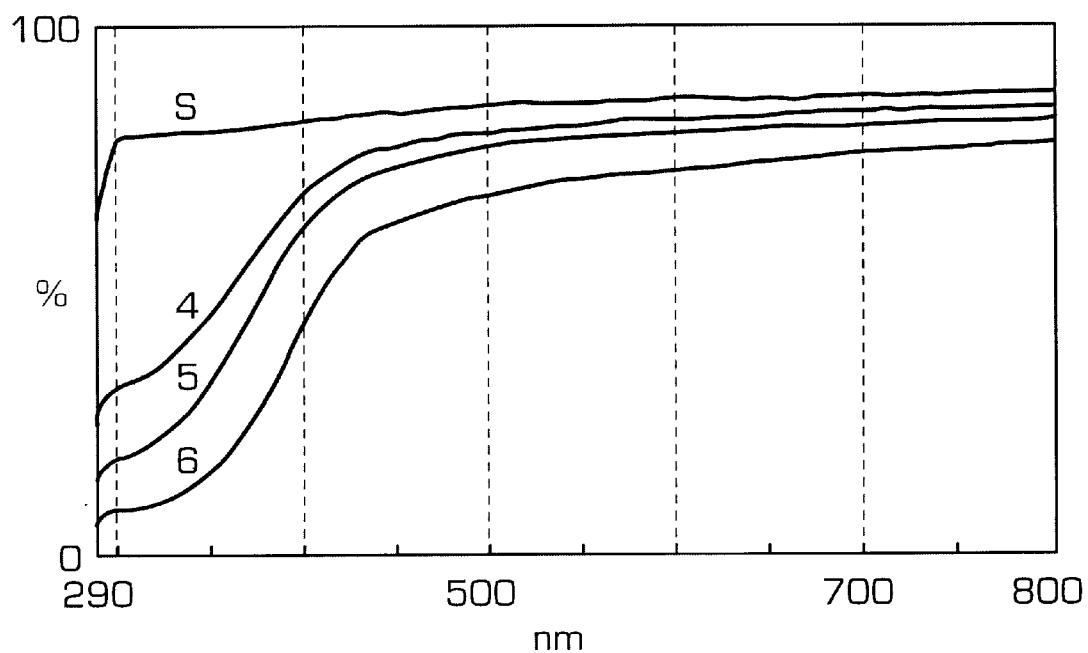

FIG. 2 is a graph of light transmission of the powder obtained in Examples.

The ordinate is a light transmission (%), and the abscissa is a wavelength (nm); S indicates the plate barium sulfate used in Examples 1 to 12; and numerals 4, 5 and 6 indicate powders obtained in Example Nos. 4, 5 and 6, respectively.

Figure 3:
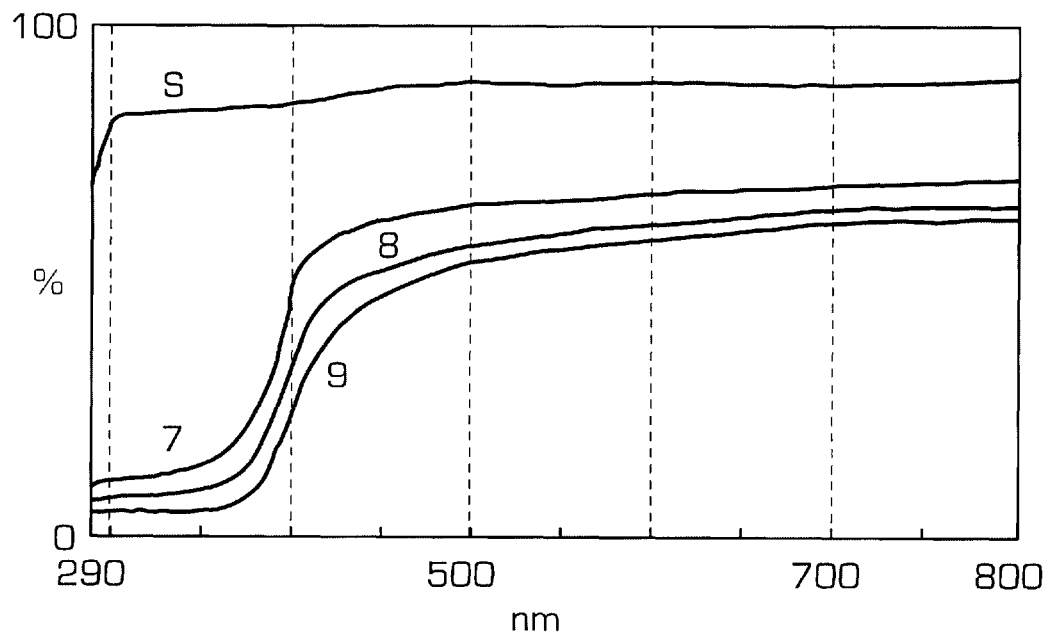

FIG. 3 is a graph of light transmission of the powder obtained in Examples.

The ordinate is a light transmission (%), and the abscissa is a wavelength (nm); S indicates the plate barium sulfate used in Examples 1 to 12; and numerals 7, 8 and 9 indicate powders obtained in Example Nos. 7, 8 and 9, respectively.

Figure 4:
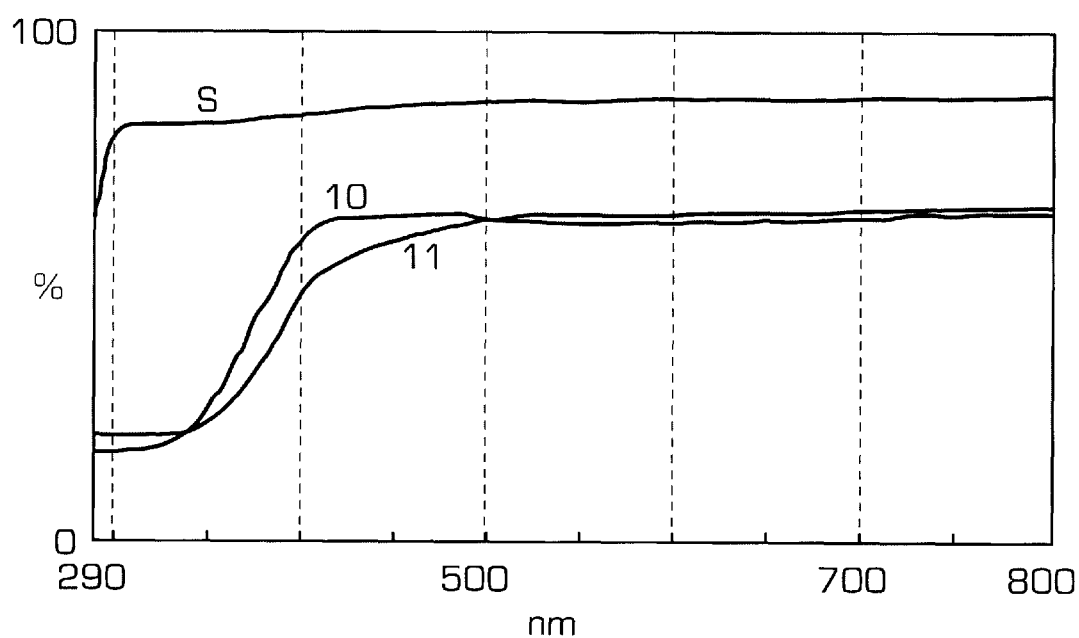

FIG. 4 is a graph of light transmission of the powder obtained in Examples.

The ordinate is a light transmission (%), and the abscissa is a wavelength (nm); S indicates the plate barium sulfate used in Examples 1 to 12; and numerals 10 and 11 indicate powders obtained in Example Nos. 10 and 11, respectively.

Figure 5:
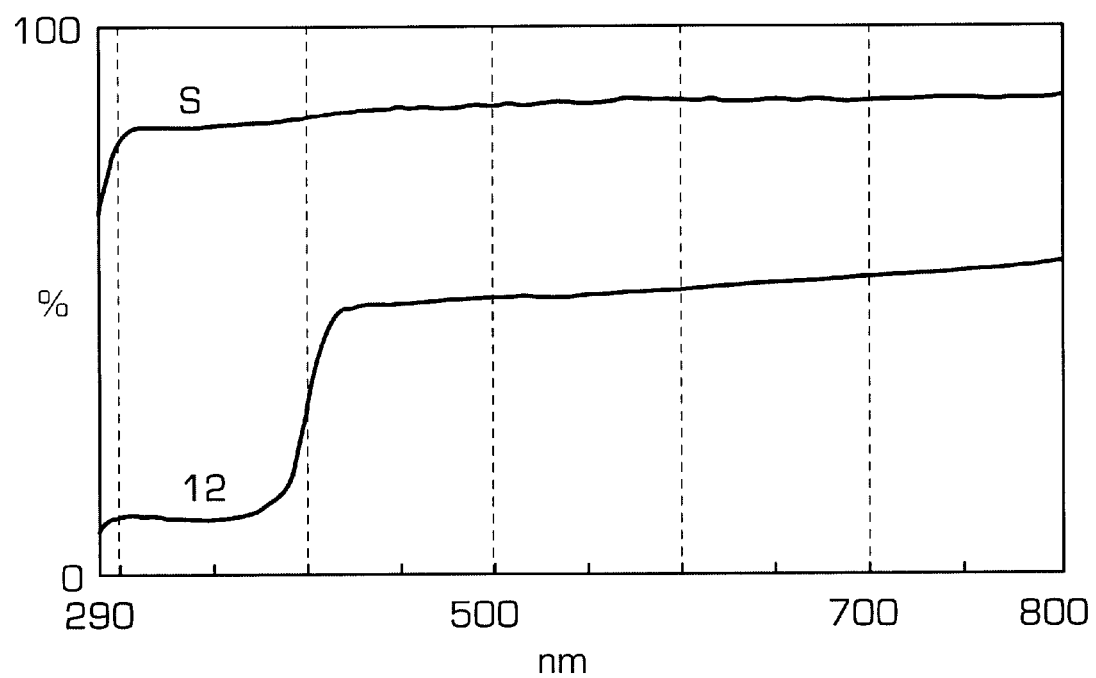

FIG. 5 is a graph of light transmission of the powders obtained in Examples.

The ordinate is a light transmission (%), and the abscissa is a wavelength (nm); S indicates the plate barium sulfate used in Examples 1 to 12; and numerals 12 indicates the powder obtained in Example No. 12.

Figure 6:
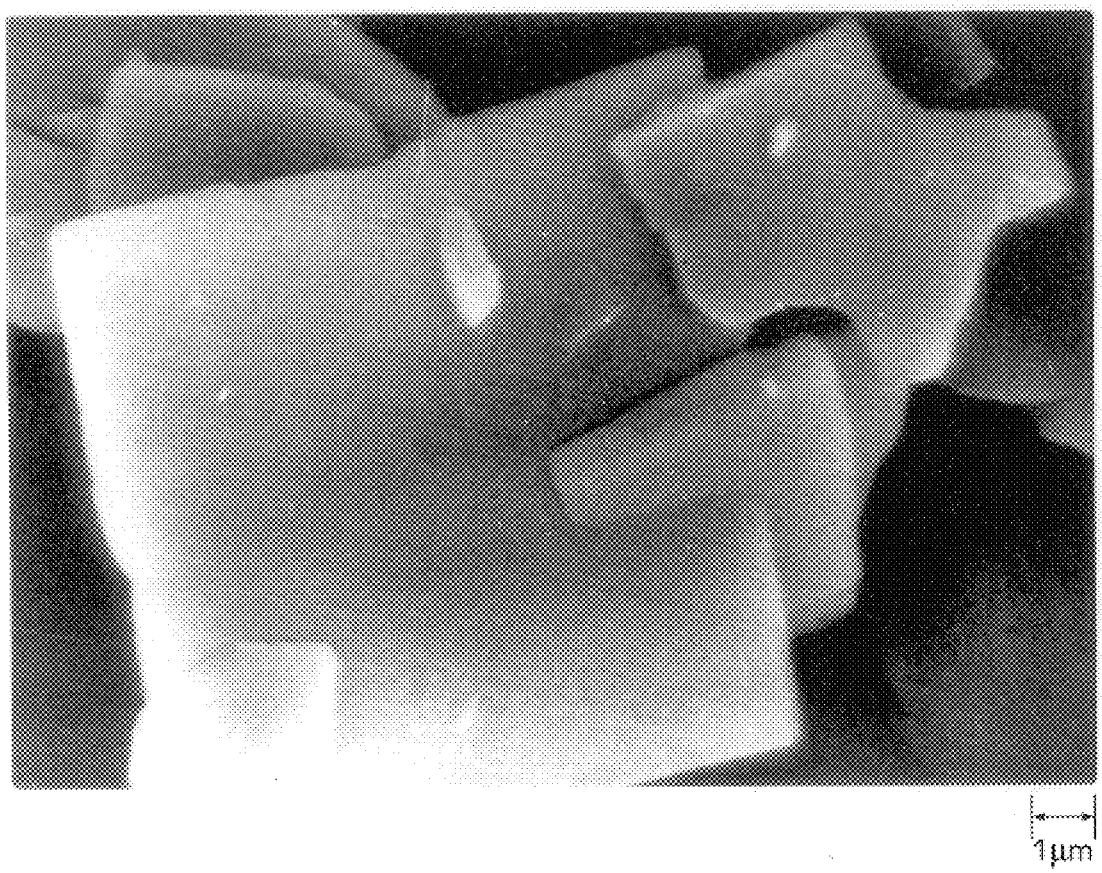

FIG. 6 is a scanning electron micrograph (×10000) of the powder obtained in Example 1.

Figure 7:
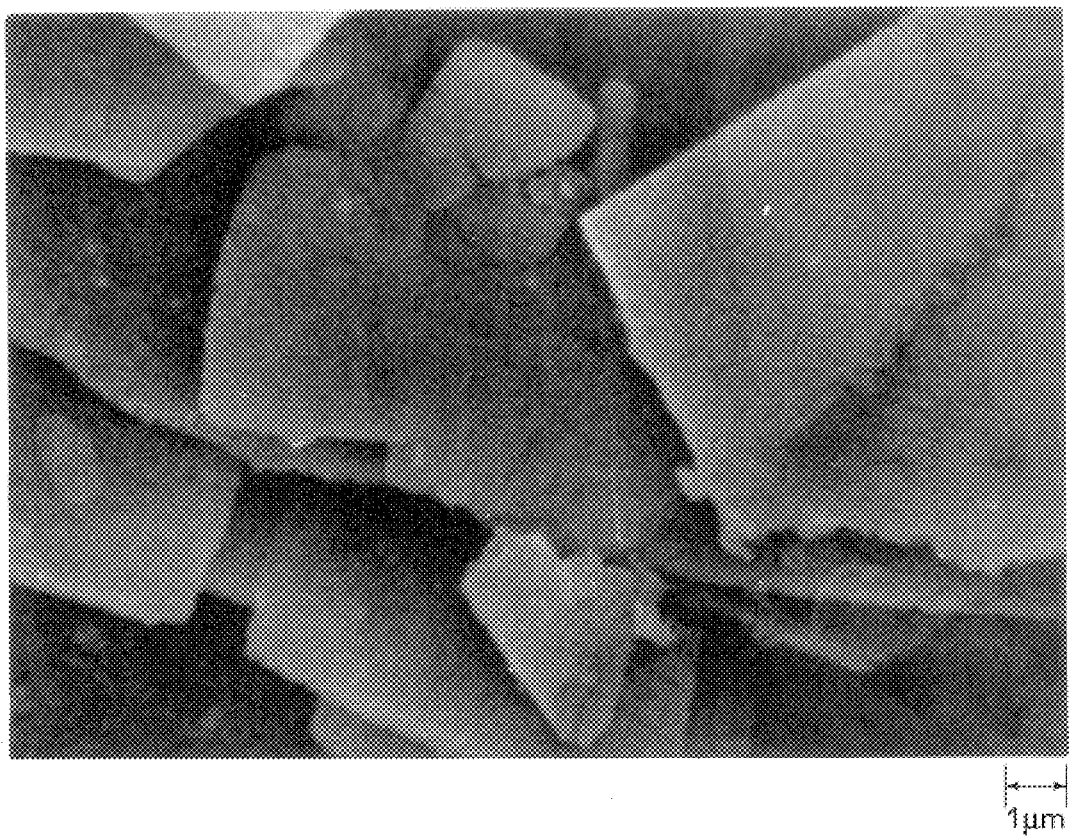

FIG. 7 is a scanning electron micrograph (×10000) of the powder obtained in Example 7.

Figure 8:
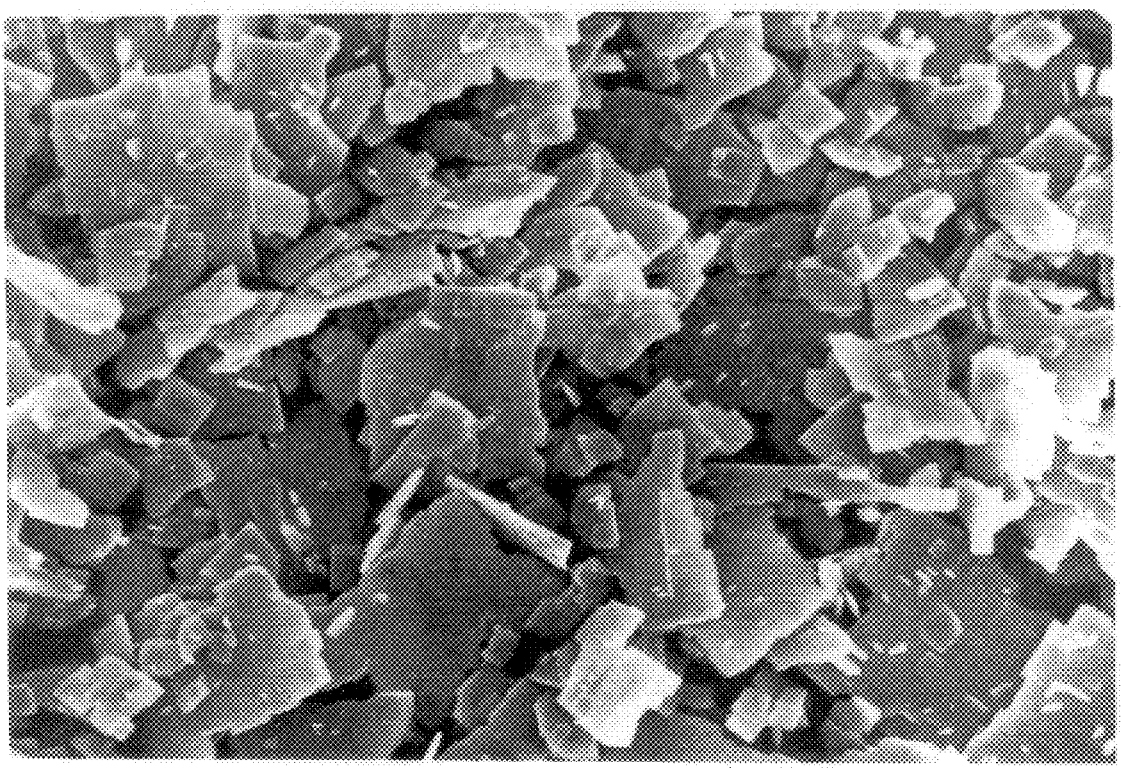

FIG. 8 is a scanning electron micrograph (×10000) of the plate barium sulfate obtained in Reference Example 1.

Figure 9:
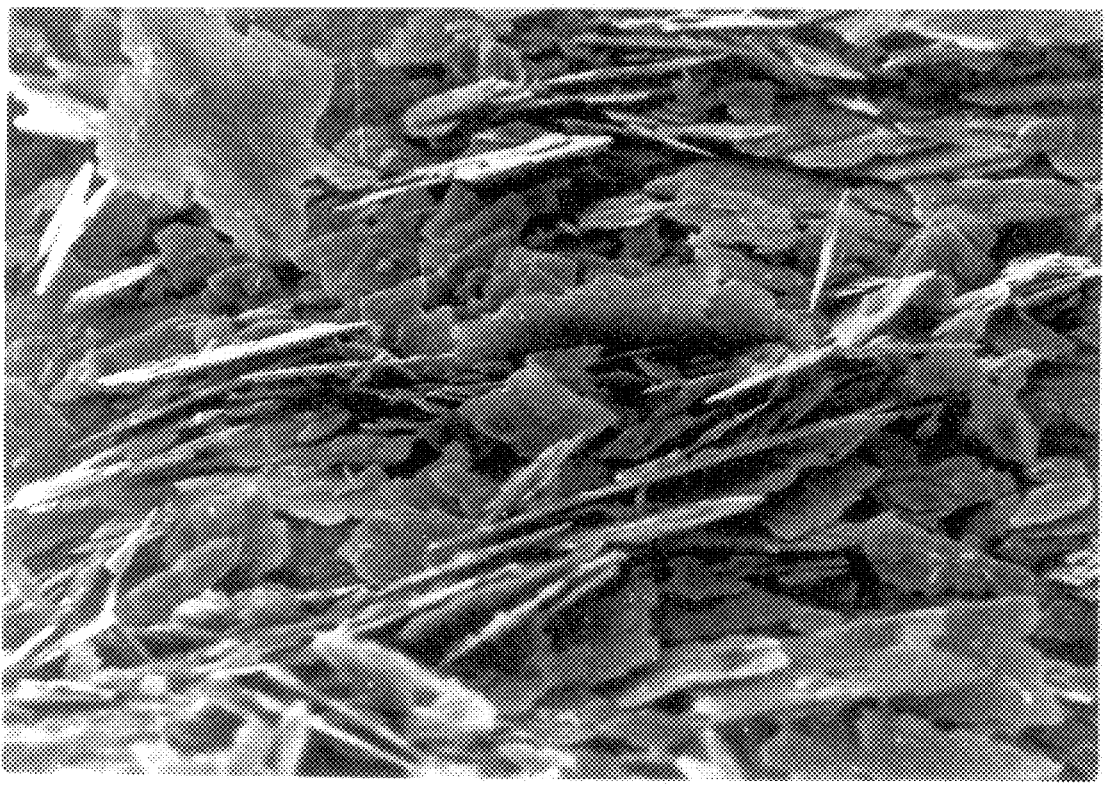

FIG. 9 is a scanning electron micrograph (×10000) taken of the same plate barium sulfate of FIG. 8 from an angle forming 90° with the angle of the micrograph of FIG. 8.

BEST MODE FOR CARRYING OUT THE INVENTION

The present invention will now be illustrated in greater detail with reference to Examples, but it should be understood that the invention is not construed as being limited thereto.

Reference Example 1

Preparation of Plate Barium Sulfate

A reaction vessel having an overflow capacity of 3 l was filled with pure water at 70° C. While stirring the water, a 65 g/l (0.663 mol/l) aqueous solution of sulfuric acid at 70° C. and a 35 g/l (0.204 mol/l) aqueous solution of barium hydroxide at 70° C. were simultaneously fed thereto continuously by using the respective microtube pumps capable of fine adjustment.

The feed rate of the sulfuric acid solution was fixed at 120 ml/min. The electric conductivity of the overflow was continuously measured, and the feed rate of the barium hydroxide solution was controlled so as to keep the electric conductivity at or below 30 $\mu$S (corresponding to the unreacted ion concentration of about 0.00003 mol/l or less). When the conductivity assumed a steady value of 30 $\mu$S, the feed rate of the barium hydroxide solution was found to be 390 ml/min.

After 10 minutes from the start of the reaction, about 500 ml of the reaction mixture was taken. The pH of the reaction mixture was about 4.0 so that a 0.1 mol/l barium hydroxide aqueous solution was added to adjust to a pH of 6.5. The reaction mixture was filtered, and the collected solid was dried at 120° C. to obtain white barium sulfate powder.

Measurement of Average Particle Diameter

Observation of the resulting barium sulfate powder under a scanning electron microscope revealed that the particles were plate. Lines were drawn on the micrograph at random, and the average of the lengths of 20 particles on the lines was calculated to obtain an average particle diameter.

Measurement of Average Particle Thickness

After the measurement of average particle diameter, the same sample was turned sideways so that the thickness direction of the barium sulfate particles might be observed. The particles were observed from this angle under a scanning electron microscope, and the average of the thicknesses of 20 particles on the lines drawn at random was calculated to obtain an average thickness.

EXAMPLE 1

Coating with Zinc Oxide

In a 2 l beaker was put 1 l of a zinc sulfate aqueous solution having a sulfuric acid concentration of 7 g/l and a zinc oxide concentration of 6 g/l and adjusted at 20° C. While stirring the solution with a stirrer, 20 g of plate barium sulfate having an average particle diameter of 30 $\mu$m and a specific surface area of 0.5 m$^2$/g was suspended therein (ZnO:BaSO$_4$=3:10 by weight).

Then, 250 ml of a 20 g/l aqueous solution of ammonia was fed to the suspension at a rate of 100 ml/min with a microtube, followed by stirring for 30 minutes. The reaction mixture was filtered using a Buchner funnel. The filter cake was washed with water until no sulfate group was detected from the washing, and dried at 120° C.

The powder was calcined in an electric oven set at 500° C. for 1 hour to obtain about 25 g of slightly yellow-tinted powder.

The resulting powder was observed under a scanning electron microscope. The micrograph (×10000) is shown in FIG. 6.

EXAMPLE 2

In the same manner as in Example 1, except for using a zinc sulfate solution having a sulfuric acid concentration of 10.1 g/l and a zinc oxide concentration of 10 g/l and increasing the amount of aqueous ammonia to be added to 360 ml (ZnO:BaSO$_4$=5:10 by weight), about 30 g of slightly yellow-tinted powder was obtained.

EXAMPLE 3

In the same manner as in Example 1, except for using a zinc sulfate solution having a sulfuric acid concentration of 20.2 g/l and a zinc oxide concentration of 20 g/l and increasing the amount of aqueous ammonia to be added to 720 ml (ZnO:BaSO$_4$=10:10 by weight), about 40 g of yellow-tinted powder was obtained.

EXAMPLE 4

In the same manner as in Example 1, except for replacing the zinc sulfate solution with a cerium sulfate solution having a sulfuric acid concentration of 5 g/l and a cerium oxide concentration of 6 g/l and changing the amount of aqueous ammonia to be added to 180 ml (CeO$_2$:BaSO$_4$=3:10 by weight), about 25 g of pale yellow powder was obtained.

EXAMPLE 5

In the same manner as in Example 4, except for using a cerium sulfate solution having a sulfuric acid concentration of 8.5 g/l and a cerium oxide concentration of 10 g/l and changing the amount of aqueous ammonia to be added to 300 ml (CeO$_2$:BaSO$_4$=5:10 by weight), about 30 g of pale yellow powder was obtained.

EXAMPLE 6

In the same manner as in Example 4, except for using a cerium sulfate solution having a sulfuric acid concentration of 17 g/l and a cerium oxide concentration of 20 g/l and changing the amount of aqueous ammonia to be added to 600 ml (CeO$_2$:BaSO$_4$=10:10 by weight), about 60 g of pale yellow powder was obtained.

EXAMPLE 7

In a 4 l beaker was put 2 l of a titanyl sulfate aqueous solution having a sulfuric acid concentration of 6 g/l and a titanium oxide concentration of 1.5 g/l. While stirring the solution with a stirrer, 10 g of the same plate barium sulfate as used in Example 1 was suspended therein (TiO$_2$:BaSO$_4$=

3:10 by weight). Then, 450 ml of a 20 g/l aqueous solution of ammonia was fed to the suspension at a rate of 200 ml/min with a microtube, followed by stirring for 30 minutes. The reaction mixture was worked up and calcined in the same manner as in Example 1 to obtain about 12 g of white powder.

The resulting powder was observed under a scanning electron microscope. The micrograph (×10000) is shown in FIG. 7.

EXAMPLE 8

In the same manner as in Example 7, except for using a titanyl sulfate solution having a sulfuric acid concentration of 10 g/l and a titanium oxide concentration of 2.5 g/l and changing the amount of aqueous ammonia to be added to 750 ml ($TiO_2$:$BaSO_4$=5:10 by weight), about 14 g of white powder was obtained.

EXAMPLE 9

In the same manner as in Example 7, except for using a titanyl sulfate solution having a sulfuric acid concentration of 20 g/l and a titanium oxide concentration of 5 g/l and changing the amount of aqueous ammonia to be added to 1500 ml ($TiO_2$:$BaSO_4$=10:10 by weight), about 18 g of white powder was obtained.

EXAMPLE 10

In a 500 ml beaker was put 375 ml of a titanium sulfate aqueous solution having a sulfuric acid concentration of 15 g/l and a titanium oxide concentration of 4 g/l and adjusted at 20° C. While stirring the solution with a stirrer, 10 g of the same plate barium sulfate as used in Example 1 was suspended therein ($TiO_2$:$BaSO_4$=1.5:10 by weight). The suspension was heated by a heater at a rate of temperature rise of 5° C./min and boiled for 2 hours. Meanwhile, pure water was added to maintain the volume of the liquid constant.

The reaction mixture was filtered using a Buchner funnel. The filter cake was washed with water until no sulfate group was detected from the washing, and dried at 120° C. The resulting powder was calcined in an electric oven set at 600° C. for 1 hour to obtain about 11 g of white powder.

The resulting powder, when spread thinly on white paper, assumed a golden pearly luster.

EXAMPLE 11

In the same manner as in Example 10, except for using a 1 l-volume beaker and changing the amount of the titanyl sulfate solution to 625 ml ($TiO_2$:$BaSO_4$=2.5:10 by weight), about 12 g of white powder was obtained.

The resulting powder, when spread thinly on white paper, assumed a reddish purple pearly luster.

EXAMPLE 12

In a 2 l beaker made of glass was put 1 l of water. While stirring the water with a stirrer, 20 g of the same plate barium sulfate as used in Example 1 and 6 g of fine titanium oxide particles having an average particle size of 50 mm (STR-60N, produced by Sakai Chemical Industry Co., Ltd.) were added thereto, followed by stirring for 30 minutes. The mixture was filtered using a Buchner funnel and dried at 120° C. to obtain about 26 g of plate barium sulfate coated with fine titanium oxide particles ($TiO_2$:$BaSO_4$).

Evaluation
Ultraviolet Rays-Sheltering Effect

The coating composition was prepared from the powder thus obtained, and the light transmission of the coated film which was spread on a transparent film was measured with V-550, U.V. VISS Pictrophotometer (produced by Nippon Bunkosha).

Sample for Measuring Light Transmission
Formulation

| Powder | 7 g |
|---|---|
| Nitrocellulose solution (nitrocellulose:isopropyl alcohol = 1:1 by weight) | 2.5 g |
| Xylene | 9 g |
| Isopropyl alcohol | 9 g |
| Butyl acetate | 9 g |
| Dioctyl phthalate | 1.2 g |
| Glass beads (diameter: 1.5 mm) | 90 g |

The above components were put in a 100 ml-volume mayonnaise bottle and dispersed with a red devil paint conditioner for 10 minutes to prepare a coating composition. The resulting coating composition was spread on a biaxially stretched transparent polypropylene film with a No. 22 bar coater and dried at room temperature.

Results of Light Transmission

The results of the light transmission of the coating film in a wavelength range of from 290 to 800 nm were shown in FIGS. 1, 2, 3, 4 and 5.

Industrial Applicability

Based on the above constitution, the present invention provides an ultraviolet rays-absorbing composition having satisfactory translucence and a fine feel. The ultraviolet rays-absorbing composition of the invention is of great use as cosmetics and coatings.

What is claimed is:

1. An ultraviolet rays-absorbing composition having a pearly luster which comprises plate barium sulfate particles having a surface coated with at least one of zinc oxide, cerium oxide and titanium oxide.

2. The ultraviolet rays-absorbing composition according to claim 1, wherein the plate barium sulfate particles have an average particle diameter of 3 to 70 μm and an average thickness of 0.05 to 2 μm.

3. The ultraviolet rays-absorbing composition according to claim 1, wherein at least one of the zinc oxide, cerium oxide and titanium oxide has a maximum particle size of not more than 0.2 μm and an average particle size of 10 to 150 nm.

4. A process for producing an ultraviolet rays-absorbing composition according to any one of claims 1, 2 and 3, which comprises:

suspending plate barium sulfate in water;

adding an aqueous solution of a zinc salt to the suspension;

adding at least one aqueous solution selected from the group consisting of aqueous ammonia, an aqueous solution of an alkali hydroxide, an aqueous solution of an alkali carbonate, an aqueous solution of ammonium carbonate and an aqueous solution of ammonium hydrogencarbonate;

obtaining plate barium sulfate particles having a surface coated with zinc oxide by filtration, washing with water, drying and calcining; and preparing a composition using the plate barium sulfate having a surface coated with zinc oxide.

5. A process for producing an ultraviolet rays-absorbing composition according to any one of claims 1, 2 and 3, which comprises:

suspending plate barium sulfate in water;

adding an aqueous solution of a cerium salt to the suspension;

adding at least one aqueous solution selected from the group consisting of aqueous ammonia, an aqueous solution of an alkali hydroxide, an aqueous solution of an alkali carbonate, an aqueous solution of ammonium carbonate and an aqueous solution of ammonium hydrogencarbonate;

obtaining plate barium sulfate particles having a surface coated with cerium oxide by filtration, washing with water, drying and calcining; and preparing a composition using the plate barium sulfate having a surface coated with cerium oxide.

6. A process for producing an ultraviolet rays-absorbing composition according to any one of claims 1, 2 and 3, which comprises:

suspending plate barium sulfate in water;

adding a titanyl sulfate aqueous solution or a titanium tetrachloride aqueous solution to the suspension;

subjecting the suspension to hydrolysis under heating or adding to the suspension at least one alkali solution selected from the group consisting of aqueous ammonia, an alkali hydroxide aqueous solution and a urea aqueous solution;

obtaining plate barium sulfate particles having a surface coated with zinc oxide by filtration, washing with water, drying and calcining; and preparing a composition using the plate barium sulfate having a surface coated with titanium oxide.

7. A process for producing an ultraviolet rays-absorbing composition according to any one of claims 1, 2 and 3, which comprises:

(A) at least one set of procedures selected from the group consisting of i) and ii) as follows:

i) at least two routines selected from the group consisting of a), b) and c) as follows:

a) suspending plate barium sulfate in water;

adding an aqueous solution of a zinc salt to the suspension; and adding at least one aqueous solution selected from the group consisting of aqueous ammonia, an aqueous solution of an alkali hydroxide, an aqueous solution of an alkali carbonate, an aqueous solution of ammonium carbonate, and an aqueous solution of ammonium hydrogencarbonate;

b) suspending plate barium sulfate in water;

adding an aqueous solution of a cerium salt to the suspension; and adding at least one aqueous solution selected from the group consisting of aqueous ammonia, an aqueous solution of an alkali hydroxide, an aqueous solution of an alkali carbonate, an aqueous solution of ammonium carbonate, and an aqueous solution of ammonium hydrogencarbonate; and c) suspending plate barium sulfate in water;

adding a titanyl sulfate aqueous solution or a titanium tetrachloride aqueous solution to the suspension; and subjecting the suspension to hydrolysis under heating or adding to the suspension at least one alkali solution selected from the group consisting of aqueous ammonia, an alkali hydroxide aqueous solution and a urea aqueous solution; and obtaining plate barium sulfate having a surface coated with at least two oxides selected from the group consisting of zinc oxide, cerium oxide and titanium oxide, by filtration, washing with water, drying and calcining; and ii) suspending plate barium sulfate in water;

adding to the aqueous suspension at least two solutions selected from the group consisting of a zinc salt aqueous solution, a cerium salt aqueous solution and a titanyl sulfate aqueous solution or a titanium tetrachloride aqueous solution;

subjecting the suspension to hydrolysis under heating or adding to the suspension at least one alkali solution selected from the group consisting of aqueous ammonia, an alkali hydroxide aqueous solution and a urea aqueous solution; and obtaining plate barium sulfate having a surface coated with at least two oxides selected from the group consisting of zinc oxide, cerium oxide and titanium oxide, by filtration, washing with water, drying and calcining; and (B) preparing a composition using the plate barium sulfate particles of (A) having a surface coated with at least two oxides selected from the group consisting of zinc oxide, cerium oxide and titanium oxide.

* * * * *